(12) United States Patent
Cresina et al.

(10) Patent No.: US 8,187,281 B2
(45) Date of Patent: May 29, 2012

(54) VARIABLE ANGLE TARGETING DEVICE

(75) Inventors: Jeffery Cresina, Middlesex, NJ (US); Timothy M. Elghazaly, Piscataway, NJ (US); Ryan Cameron Lakin, Newton, NJ (US)

(73) Assignee: EBI, LLC, Parsippany, NJ (US)

( * ) Notice: Subject to any disclaimer, the term of this patent is extended or adjusted under 35 U.S.C. 154(b) by 848 days.

(21) Appl. No.: 12/244,433

(22) Filed: Oct. 2, 2008

(65) Prior Publication Data

US 2009/0099571 A1 Apr. 16, 2009

Related U.S. Application Data

(60) Provisional application No. 60/978,817, filed on Oct. 10, 2007.

(51) Int. Cl.
*A61B 17/58* (2006.01)

(52) U.S. Cl. ........................................................ 606/96

(58) Field of Classification Search .............. 606/54–60, 606/62–64, 86 R, 96, 98, 102, 104; 403/113, 403/116, 117, 161; 248/183.2, 278.1, 538, 248/540, 541

See application file for complete search history.

(56) References Cited

U.S. PATENT DOCUMENTS

| | | | |
|---|---|---|---|
| 4,881,535 A | 11/1989 | Sohngen | |
| 4,911,153 A | 3/1990 | Border | |
| 5,078,355 A * | 1/1992 | Fujimoto et al. | 248/183.2 |
| 5,281,224 A | 1/1994 | Faccioli et al. | |
| 5,295,991 A | 3/1994 | Frigg et al. | |
| 5,346,496 A | 9/1994 | Pennig et al. | |
| 5,433,720 A | 7/1995 | Faccioli et al. | |
| 6,514,253 B1 | 2/2003 | Yao et al. | |
| 6,579,293 B1 | 6/2003 | Chandran | |
| 6,916,323 B2 | 7/2005 | Kitchens | |
| 6,958,067 B2 * | 10/2005 | Whittaker et al. | 606/98 |
| 7,056,322 B2 | 6/2006 | Davison et al. | |

FOREIGN PATENT DOCUMENTS

| | | |
|---|---|---|
| CH | 668692 | 1/1989 |
| EP | 0514662 | 11/1992 |
| WO | WO-9201422 | 2/1992 |
| WO | WO-03065907 A1 | 8/2003 |

OTHER PUBLICATIONS

European Search Report mailed Apr. 19, 2010 for EP08017737.
European Search Report Opinion mailed Apr. 19, 2010 for EP08017737.

* cited by examiner

*Primary Examiner* — Thomas C. Barrett
*Assistant Examiner* — Christian Sevilla
(74) *Attorney, Agent, or Firm* — Harness, Dickey (57) ABSTRACT

An orthopedic device includes a targeting member, an elongated guiding member, and an adjustment member. The targeting member has an elongated body along a first longitudinal axis and can be coupled to an intramedullary implant such that the first longitudinal axis is parallel to the intramedullary implant. The targeting member includes a first bore extending along a second longitudinal axis t1hrough the elongated body, the first bore having a cross-section elongated in the direction of the first longitudinal axis. The first and second longitudinal axes define a first plane. The elongated guiding member passes through the first bore and is pivotable relative to the first longitudinal axis. The adjustment member is coupled to the elongated body and operable to change an orientation of the guiding member relative to the first longitudinal axis in the first plane.

16 Claims, 6 Drawing Sheets

VARIABLE ANGLE TARGETING DEVICE

CROSS-REFERENCE TO RELATED APPLICATIONS

This application claims the benefit of U.S. Provisional Application No. 60/978,817, filed on Oct. 10, 2007. The disclosure of the above application is incorporated herein by reference.

INTRODUCTION

Various targeting/aiming systems are known and used in orthopedic fixation applications to position implants and bone fasteners in precise locations.

The present teachings provide a device that allows variable angle targeting for bone fasteners and can be used with various targeting systems.

SUMMARY

The present teachings provide an orthopedic device for use with a targeting system for intramedullary fixation. The orthopedic device can provide a variable angle orientation for guiding members of the targeting system. In one aspect, the orthopedic device can provide variable angular orientation in more than one sagittal plane relative to an intramedullary implant.

In one aspect, the present teachings provide an orthopedic device that includes a targeting member, an elongated guiding member, and an adjustment member. The targeting member has an elongated body along a first longitudinal axis and can be coupled to an intramedullary implant such that the first longitudinal axis is parallel to the intramedullary implant. The targeting member includes a first bore extending along a second longitudinal axis through the elongated body, the first bore having a cross-section elongated in the direction of the first longitudinal axis. The first and second longitudinal axes define a first plane. The elongated guiding member passes through the first bore and is movable relative to the first longitudinal axis. The adjustment member is coupled to the elongated body and operates to change an orientation of the guiding member relative to the first longitudinal axis in the first plane.

In another aspect, the present teachings provide an orthopedic device that includes a targeting member couplable to an intramedullary implant, the targeting member including a body defining a first bore having an elongated cross-section and a second bore transversely intersecting the first bore. The orthopedic device also includes a guiding member passing through the first bore, the guiding member movable in a first plane parallel to the intramedullary implant and not intersecting the intramedullary implant. An adjustment member is pivotably coupled to the body and has a shaft received in the second bore of the targeting member. The shaft has a third bore transverse to the shaft, the third bore receiving the guiding member, such that rotation of the adjustment member changes the orientation of the guiding member relative to the intramedullary implant in the first plane.

The present teachings also provide an orthopedic device that includes an intramedullary implant, a targeting member coupled to the intramedullary implant, the targeting member including a body having first and second bores having elongated cross-sections, and first and second guiding members passing through the corresponding first and second bores. The first and second guiding members can move in first and second planes parallel to the intramedullary implant and not intersecting the intramedullary implant. The orthopedic device also includes a first adjustment member coupled to the targeting member, the first adjustment member pivotable along a first curved slot relative to the targeting member, such that rotation of the first adjustment member changes an orientation of the first guiding member relative to the intramedullary implant in the first plane. The orthopedic device also includes a second adjustment member coupled to the targeting member, the second adjustment member pivotable along a second curved slot relative to the targeting member, such that rotation of the second adjustment member changes an orientation of the second guiding member relative to the intramedullary implant in the second plane. Further, the orthopedic device includes a first locking member coupled to the first adjustment member and to the targeting member for locking the orientation of the first guiding member, and a second locking member coupled to the second adjustment member and to the targeting member for locking the orientation of the second guiding member.

Further areas of applicability of the present teachings will become apparent from the description provided hereinafter. It should be understood that the description and specific examples are intended for purposes of illustration only and are not intended to limit the scope of the present teachings.

BRIEF DESCRIPTION OF THE DRAWINGS

The present teachings will become more fully understood from the detailed description and the accompanying drawings, wherein.

DESCRIPTION OF VARIOUS ASPECTS

The following description is merely exemplary in nature and is in no way intended to limit the present teachings, applications, or uses. For example, although the present teachings are illustrated in FIGS. 7 and 8 for applications in ankle arthrodesis, the present teachings can be used with any targeting system used in other orthopedic procedures.

Referring to FIGS. 1-6, an exemplary variable angle targeting device 100 according to the present teachings can include a rotatable adjustment member 106, a locking member 108, a locking shaft 114 that can be threadably engaged with the locking member 108, and a spring-loaded plunger 110 coupled to a supporting body 102. The body 102 can have first and second opposing surfaces 220 and 222, and third and fourth opposing surfaces 224, 226. The variable angle targeting device 100 can be coupled to one or both of the first and second surfaces 220, 222 of the body 102 with a corresponding adjustment member 106, a locking member 108, and a spring-loaded plunger 110. The variable angle targeting device 100 can also include one or more tubular guiding members 200, which can be soft tissue sleeves, drilling guide sleeves or other aiming devices. The body 102 can be a portion of an orthopedic targeting/aiming system, such as an integral portion of a targeting member 210 shown in FIGS. 7 and 8, or a separate support component. Accordingly, the variable angle targeting device 100 can be positioned on one of or on both the lateral and medial sides of the targeting member 210, corresponding to the first and second surfaces 220, 222 of the body 102. Such dual positioning of the variable angle targeting device 100 can provide the surgeon with greater flexibility.

Figure 7:
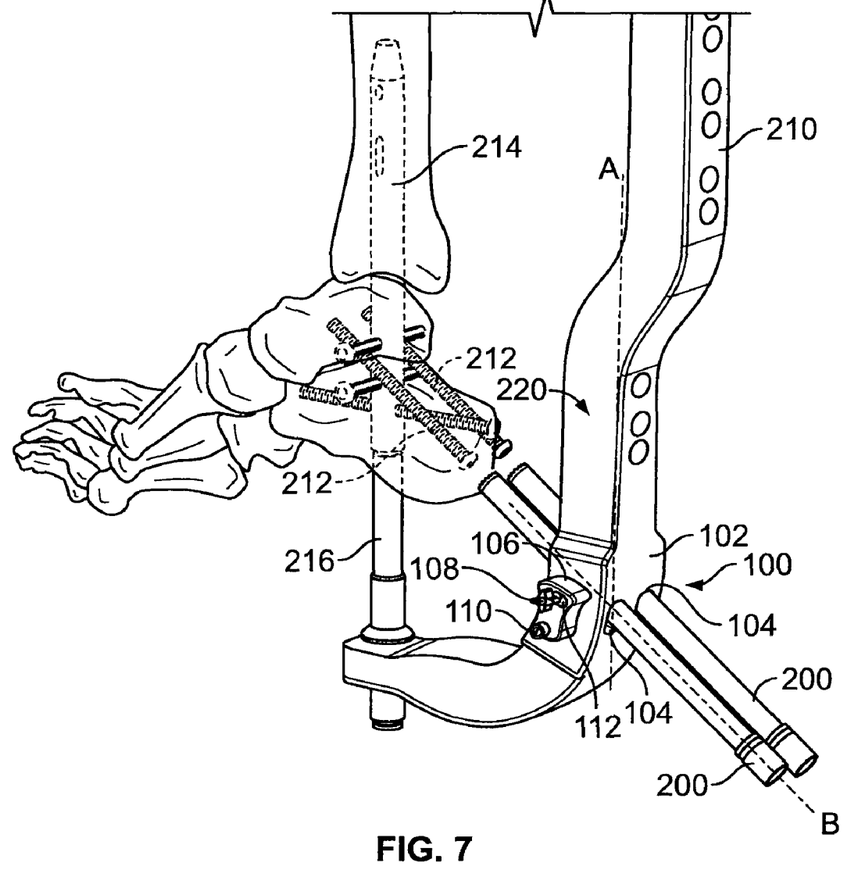
FIG. 7 is an environmental isometric view of the device of FIG. 1, shown in the environment of a targeting system for ankle arthrodesis.
Figure 8:
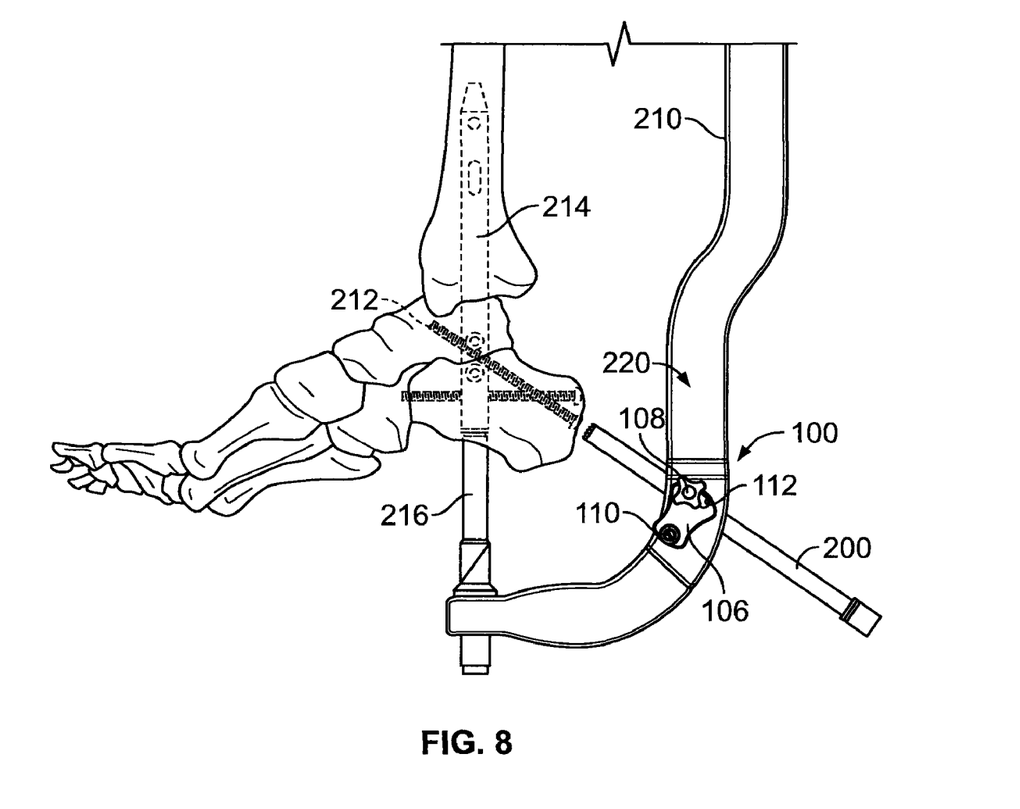
FIG. 8 an environmental front view of the device of FIG. 1, shown in the environment of a targeting system for ankle arthrodesis.

In the ankle arthrodesis procedure illustrated in FIGS. 7 and 8, for example, the surgeon can place cortical screws to fuse the ankle and the subtalar joints independently. Although dual positioning of the variable angle targeting device 100 is illustrated throughout FIGS. 1-8, it will be appreciated that single positioning on one of the first or second surfaces 220, 222 can also be used. In the sequel, only one set of the various parts of the variable angle targeting device 100 is described, with the understanding that a second set, which can be used for dual positioning, is similar. For orientation purposes in relation to the targeting system of FIG. 7, the surfaces 220, 222, 224, 226 are referenced as lateral surface 220, medial surface 222, anterior surface 224 and posterior surface 226, and the variable angle targeting device 100 is described in reference to the lateral position shown in FIG. 7.

Figure 1:
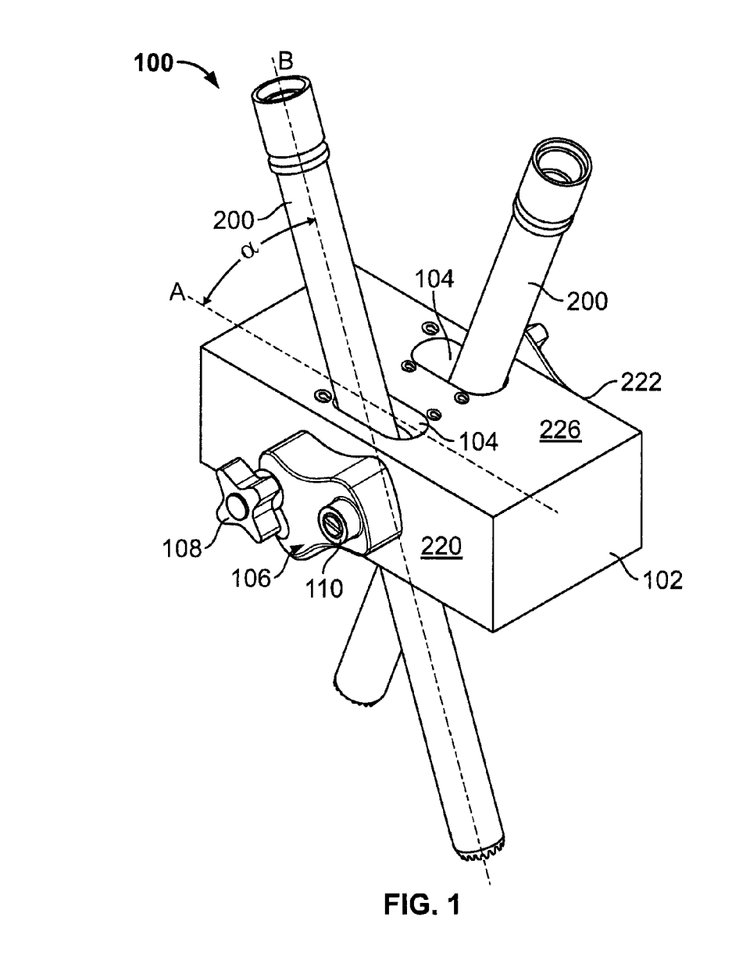
FIG. 1 is an isometric view of a variable angle targeting device according to the present teachings.
Figure 1A:
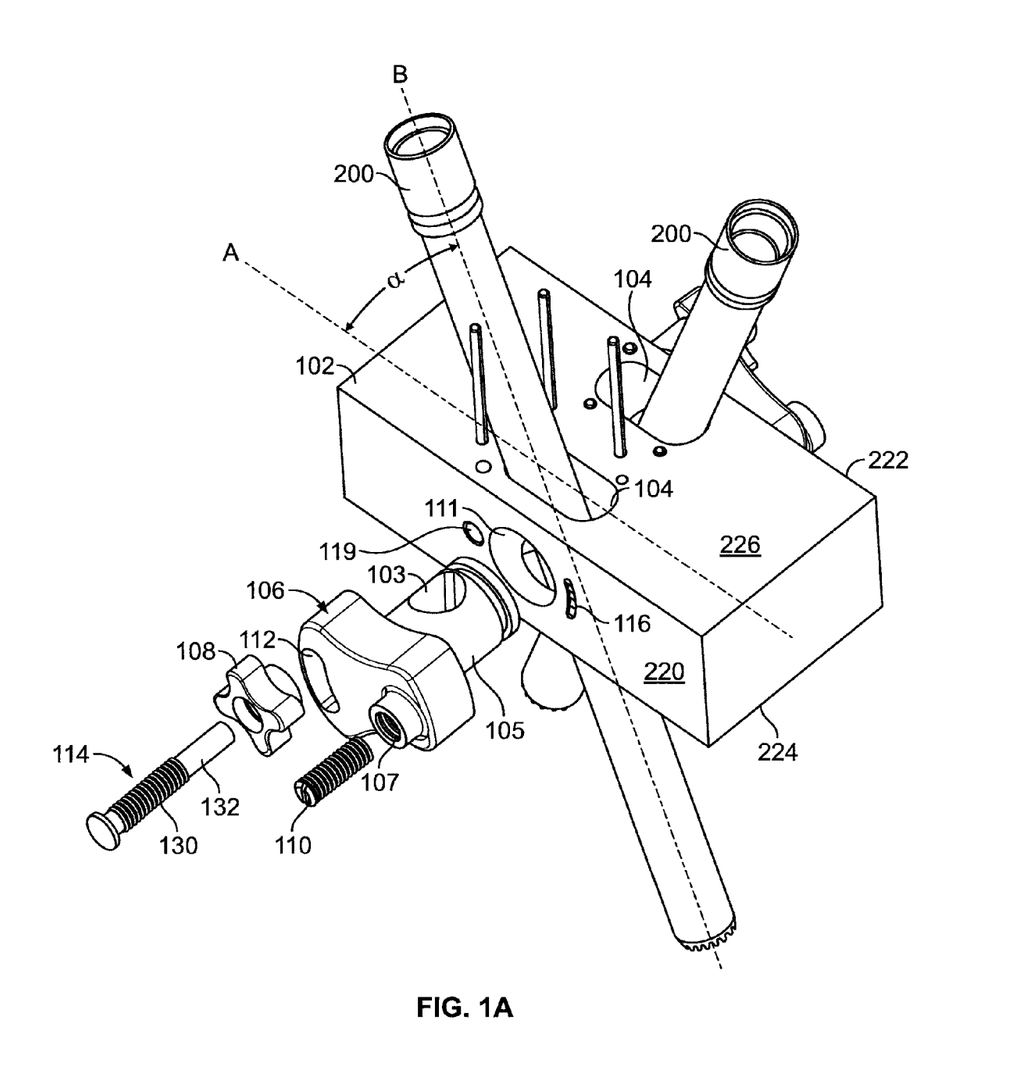
FIG. 1A is a partially exploded view of the device of FIG. 1.
Figure 2:
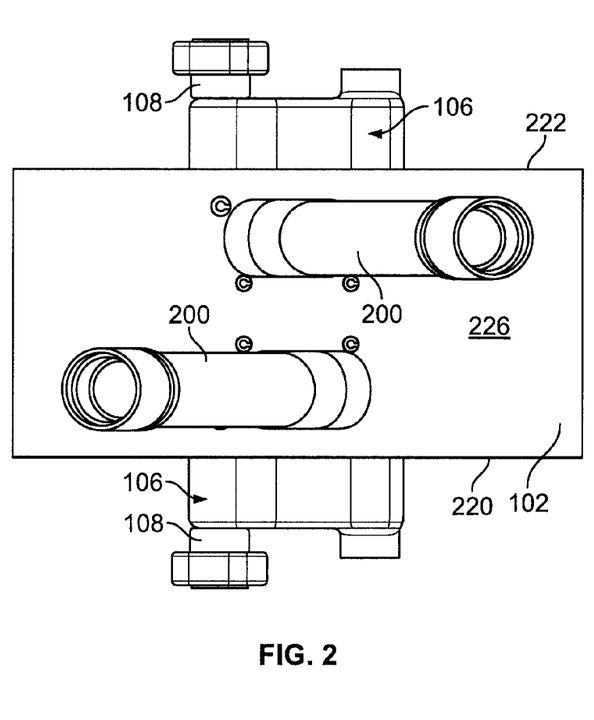
FIG. 2 is a top view of the device of FIG. 1.
Figure 3:
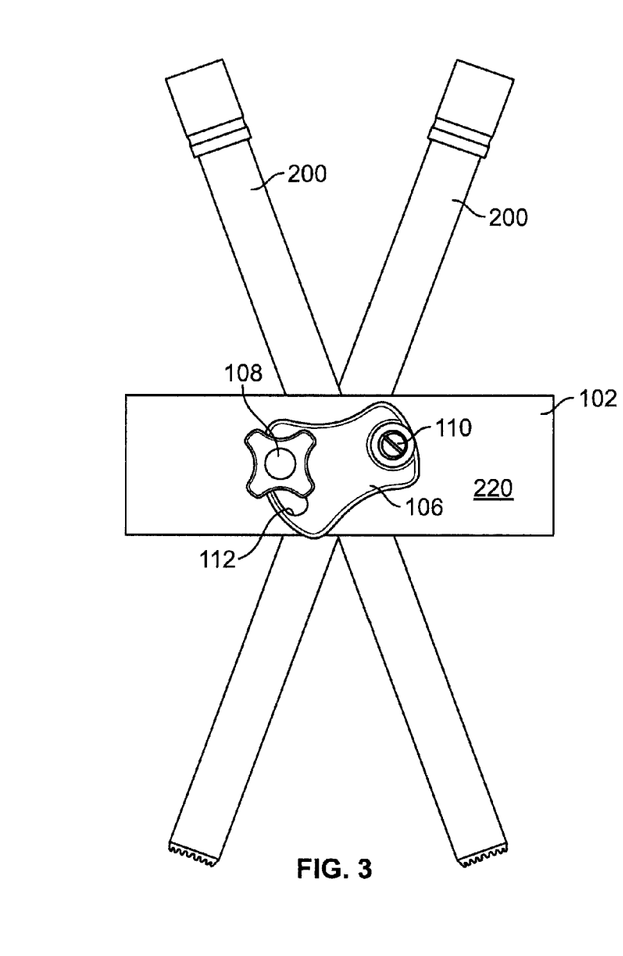
FIG. 3 is a front view of the device of FIG. 1.
Figure 4:
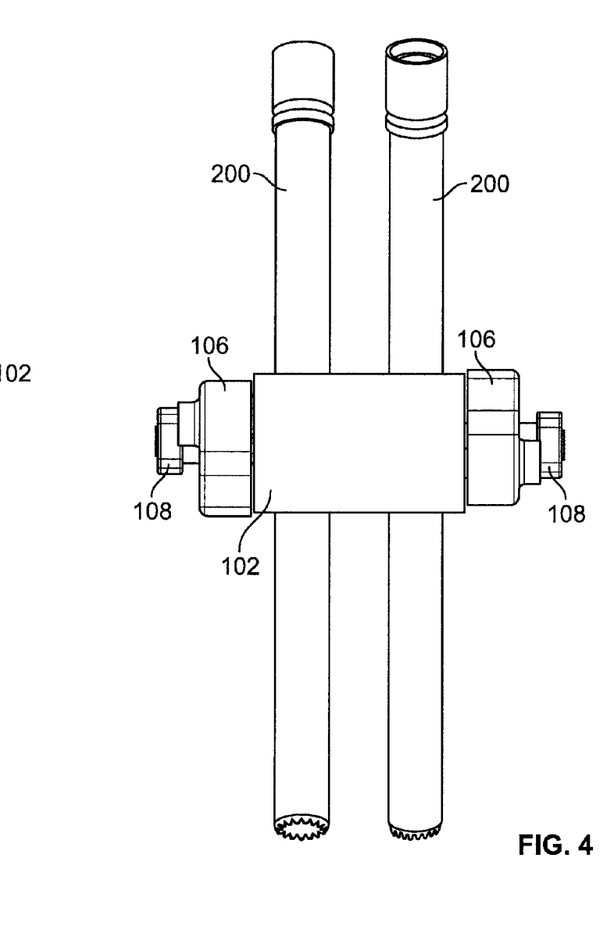
FIG. 4 is a side view of the device of FIG. 1.
Figure 5:
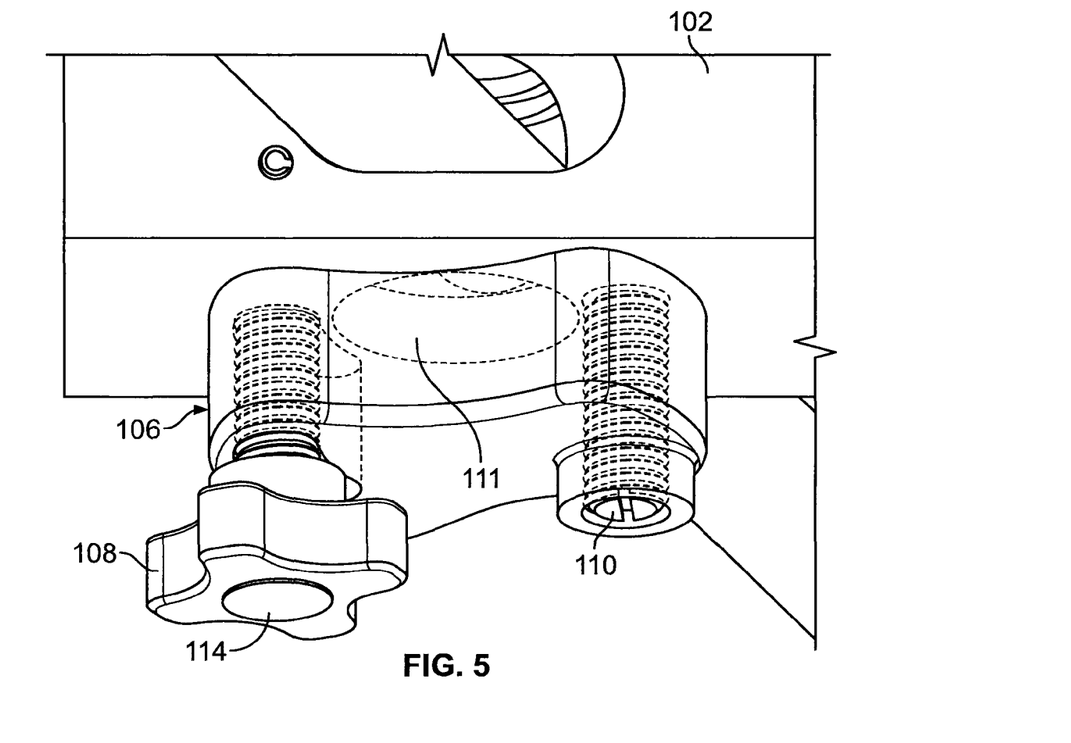
FIG. 5 is a top and side isometric view detail of FIG. 1.
Figure 6:
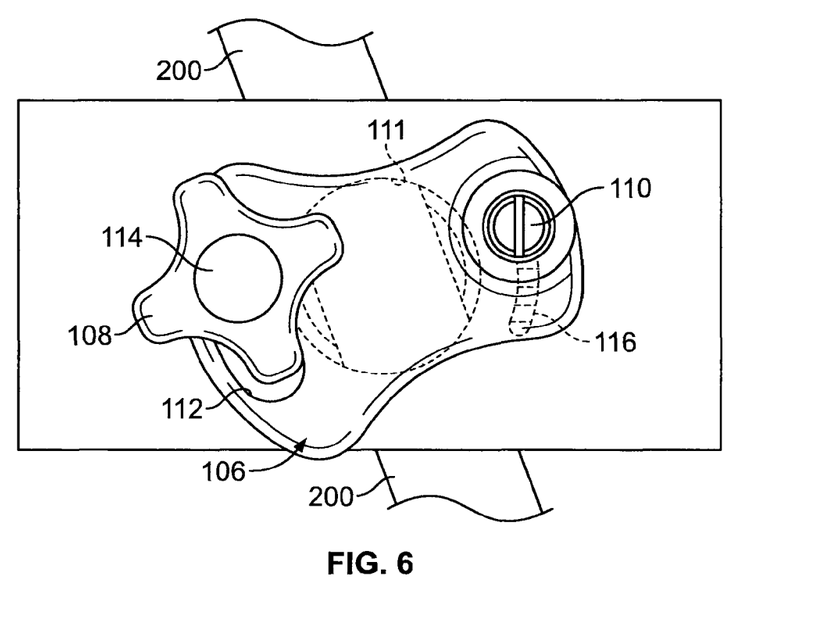
FIG. 6 is a front view detail of FIG. 1.

Referring to FIG. 1A, the body 102 can have an elongated through-slot 104, through which the guiding member 200 can pass from the posterior surface 226 to the anterior surface 224 of the body 102. The elongated slot 104 can have a cross-section elongated along an axial direction A. The body 102 can also have a side or lateral opening 110 communicating transversely with the elongated slot 104. The adjustment member 106 can include a shaft portion 105 having a transverse hole 103. The shaft portion 105 can be inserted through the side opening 111 of the body 102 and can be rotatably coupled to the body, such that the guiding member 200 can pass through the transverse hole 103. Rotating the adjustment member 106, which can be knob-like for manual rotation, can change the orientation of the guiding member 200 relative to the axial direction A, such that an angle α defined between the axial axis A and a longitudinal axis B of the guiding member 200 can be selectively changed.

The adjustment member 106 can include a curved slot 112. The locking shaft 114 can include a threaded portion 130 and an unthreaded portion 132. The locking shaft 114 can pass through the locking member 108 and through the curved slot 112 of the adjustment member 106, and can be inserted into a hole 119 of the body 102. With the locking member 108 not tightened, the adjustment member 108 can swing relative to the locking shaft 112 along the curved slot 112. As the adjustment member 106 rotates, the orientation of the guiding member 200 and the angle α defined the axial axis A and the longitudinal axis B of the guiding member 200 can change. The locking member 108 can be threadably tightened in the locking shaft 114, until it presses the adjustment member 106 against the body 102 to prevent further movement of the adjustment member 106 and secure the orientation of the guiding member 200 at a selected angle.

The adjustment member 106 can include an opening 107 threadably receiving a spring-loaded ball plunger 110. The ball plunger 110 can interact with a series of detents 116 defined along a curve on the lateral surface 220 of the body 102. The detents 116 can be equally spaced and configured to provide graduated increments indicating to the user the degree of angular adjustment or change of the guiding member 200. Thus, when the adjustment member 106 moves along the curved slot 112, the plunger 110 interfaces with the detents 116 producing an audible and tactile feedback to the user. The extent of the slot 112 can provide upper and lower limits for the degree of adjustment available.

Referring to FIGS. 7 and 8, and as described above, the variable angle device 100 can be used with various targeting systems to provide angular adjustability for guiding members 200 to allow the placement of various stabilization screws, cortical screws, transverse screws and other bone fasteners 212 at a desired orientation in a sagittal plane. The targeting system can include for example, a connecting shaft 216 that can be attached to an internal fixation implant 214, such an intramedullary nail or other fixation implant. The targeting member 210 can be rotatably coupled to the connecting shaft 216 sweeping a transverse plane that is substantially perpendicular to the intramedullary nail 214 and to the axial axis A of the targeting member 210.

The variable angle device 100 can provide additional angular adjustability by allowing angulation on a sagittal plane defined by axes A and B. Additionally, using dual positioning and placing variable angle devices 100 on both the lateral surface 220 and the medial surface 222 of the targeting member 210, two guiding members 200 can be angulated independently of one another, thereby allowing independent fixation of bone fasteners in two different positions, for ankle and talar joints, for example, when used with an ankle targeting system for ankle arthrodesis. Further, the variable angle device 100 can provide variable sagittal alignment for stabilization screws 212 that do not pass through the intramedullary nail 214, but are positioned laterally and medially outside the intramedullary nail 214.

The foregoing discussion discloses and describes merely exemplary arrangements of the present teachings. Furthermore, the mixing and matching of features, elements and/or functions between various embodiments is expressly contemplated herein, so that one of ordinary skill in the art would appreciate from this disclosure that features, elements and/or functions of one embodiment may be incorporated into another embodiment as appropriate, unless described otherwise above. Moreover, many modifications may be made to adapt a particular situation or material to the present teachings without departing from the essential scope thereof. One skilled in the art will readily recognize from such discussion, and from the accompanying drawings and claims, that various changes, modifications and variations can be made therein without departing from the spirit and scope of the present teachings as defined in the following claims.

What is claimed is:

1. An orthopedic device comprising:
a targeting member having an elongated body along a first longitudinal axis, the targeting member couplable to an intramedullary implant such that the first longitudinal axis is parallel to the intramedullary implant, the targeting member including a first bore and a second bore that intersects the first bore, the first bore extending along a second longitudinal axis through the elongated body, the first bore having a cross-section elongated in the direction of the first longitudinal axis, the first and second longitudinal axes defining a first plane;
an elongated guiding member passing through the first bore and movable relative to the first longitudinal axis;
an adjustment member pivotally coupled to the elongated body and movable along a curved slot, such that rotation of the adjustment member changes the orientation of the guiding member in the first plane, the adjustment member including a shaft that is received in the second bore, the shaft having a transverse bore therethrough, the transverse bore receiving the guiding member; and a locking member coupled to the adjustment member and a locking shaft passing through the locking member and through the curved slot and insertable into a hole of the elongated body.

2. The orthopedic device of claim 1, further comprising a spring-loaded ball plunger threadably received in an opening of the adjustment member, the ball plunger interacting with a plurality of detents defined along a curve on the elongated body.

3. The orthopedic device of claim 2, wherein the detents are spaced and configured for indicating a change in orientation of the guiding member when the adjustment member moves along the curved slot.

4. The orthopedic device of claim 1, wherein the first plane is parallel to and not intersecting the intramedullary implant when the targeting member is coupled to the intramedullary implant.

5. The orthopedic device of claim 4, further comprising an intramedullary implant.

6. An orthopedic device comprising:

a targeting member couplable to an intramedullary implant, the targeting member including a body defining a first bore having an elongated cross-section and a second bore transversely intersecting the first bore;

a guiding member passing through the first bore, the guiding member movable in a first plane parallel to the intramedullary implant and not intersecting the intramedullary implant;

an adjustment member pivotably coupled to the body and having a shaft received in the second bore of the targeting member, the shaft having a third bore transverse to the shaft, the third bore receiving the guiding member, such that rotation of the adjustment member changes the orientation of the guiding member relative to the intramedullary implant in the first plane, wherein the adjustment member is movable along a curved slot, such that rotation of the adjustment member changes the orientation of the guiding member in the first plane; and a locking member coupled to the adjustment member and a locking fastener passing through the locking member and through the curved slot and insertable into a hole of the body.

7. The orthopedic device of claim 6, further comprising a spring-loaded ball plunger threadably received in an opening of the adjustment member, the ball plunger interacting with a plurality of detents defined along a curve of the body.

8. The orthopedic device of claim 7, wherein the detents are spaced and configured for indicating a change in orientation of the guiding member when the adjustment member moves along the curved slot.

9. The orthopedic device of claim 6, further comprising an intramedullary implant.

10. An orthopedic device comprising:

an intramedullary implant;

a targeting member coupled to the intramedullary implant, the targeting member including a body having first and second bores having elongated cross-sections;

first and second guiding members passing through the corresponding first and second bores, the first and second guiding members movable in first and second planes parallel to the intramedullary implant and not intersecting the intramedullary implant;

a first adjustment member coupled to the targeting member, the first adjustment member pivotable along a first curved slot relative to the targeting member, such that rotation of the first adjustment member changes an orientation of the first guiding member relative to the intramedullary implant in the first plane;

a second adjustment member coupled to the targeting member, the second adjustment member pivotable along a second curved slot relative to the targeting member, such that rotation of the second adjustment member changes an orientation of the second guiding member relative to the intramedullary implant in the second plane;

a first locking member coupled to the first adjustment member and to the targeting member for locking the orientation of the first guiding member; and a second locking member coupled to the second adjustment member and to the targeting member for locking the orientation of the second guiding member.

11. The orthopedic device of claim 10, further comprising a first locking fastener passing through the first locking member and through the first curved slot and insertable into a first hole of the body.

12. The orthopedic device of claim 11, further comprising a first spring-loaded ball plunger threadably received in a first opening of the adjustment member, the first ball plunger interacting with a first plurality of detents defined along a first curve of the body.

13. The orthopedic device of claim 12, further comprising a second locking fastener passing through the second locking member and through the second curved slot and insertable into a second hole of the body.

14. The orthopedic device of claim 13, further comprising a second spring-loaded ball plunger threadably received in a second opening of the adjustment member, the second ball plunger interacting with a second plurality of detents defined along a second curve of the body.

15. The orthopedic device of claim 10, wherein the first and second adjustment members are positioned on opposite outer surfaces of the targeting member.

16. The orthopedic device of claim 10, wherein the targeting member is rotatable about the intramedullary implant.

* * * * *

UNITED STATES PATENT AND TRADEMARK OFFICE
CERTIFICATE OF CORRECTION

PATENT NO. : 8,187,281 B2
APPLICATION NO. : 12/244433
DATED : May 29, 2012
INVENTOR(S) : Jeffrey Cresina et al.

It is certified that error appears in the above-identified patent and that said Letters Patent is hereby corrected as shown below:

Title Page, item (57), Abstract, line 7, "t1hrough" should be --through--.

Column 2, line 43, after "FIG. 8" insert --is--.

Column 3, line 51, "locking shaft 112" should be --locking shaft 114--.

Column 4, line 12, after "such" insert --as--.

Signed and Sealed this
Seventeenth Day of July, 2012

David J. Kappos
*Director of the United States Patent and Trademark Office*